US006815063B1

(12) United States Patent
Mayes

(10) Patent No.: US 6,815,063 B1
(45) Date of Patent: Nov. 9, 2004

(54) MAGNETIC FLUID

(75) Inventor: Eric Mayes, Bristol (GB)

(73) Assignee: NanoMagnetics, Ltd., Bristol (GB)

( * ) Notice: Subject to any disclaimer, the term of this patent is extended or adjusted under 35 U.S.C. 154(b) by 67 days.

(21) Appl. No.: 10/148,228

(22) PCT Filed: Nov. 27, 2000

(86) PCT No.: PCT/GB00/04517

§ 371 (c)(1),
(2), (4) Date: May 24, 2002

(87) PCT Pub. No.: WO01/39217

PCT Pub. Date: May 31, 2001

Related U.S. Application Data

(63) Continuation-in-part of application No. 09/730,117, filed on Dec. 5, 2000, now Pat. No. 6,713,173, which is a continuation of application No. 09/308,166, filed on Jun. 25, 1999, application No. 10/148,228, which is a continuation-in-part of application No. 09/308,166, filed as application No. PCT/GB97/03152 on Nov. 17, 1997.

(30) Foreign Application Priority Data

Nov. 16, 1996 (GB) .............................................. 9623851
Nov. 25, 1999 (GB) .............................................. 9927911

(51) Int. Cl.$^7$ ................................................. G11B 5/66
(52) U.S. Cl. ........................ 428/402; 478/403; 478/407; 478/692; 252/62.52; 252/62.62; 252/62.54
(58) Field of Search ................................. 428/402, 403, 428/407, 652; 252/62.52, 62.62, 62.54

(56) References Cited

U.S. PATENT DOCUMENTS

| | | |
|---|---|---|
| 3,951,904 A | 4/1976 | Tomonaga |
| 3,966,510 A | 6/1976 | Aonuma et al. |
| 4,009,111 A | 2/1977 | Tamai et al. |
| 4,096,040 A | 6/1978 | Grosko |
| 4,123,675 A | 10/1978 | Moskowitz et al. |
| 4,269,826 A | 5/1981 | Zimmermann et al. |
| 4,361,879 A | 11/1982 | Dubbelday et al. |
| 4,384,761 A | 5/1983 | Brady et al. |
| 4,425,261 A | 1/1984 | Stenius et al. |
| 4,452,773 A | 6/1984 | Molday |
| 4,454,234 A | 6/1984 | Czerlinski |
| 4,480,256 A | 10/1984 | Wren |
| 4,672,040 A | 6/1987 | Josephson |
| 4,673,997 A | 6/1987 | Gowda et al. |
| 4,692,826 A | 9/1987 | Raj et al. |
| 4,735,796 A | 4/1988 | Gordon |
| 4,778,671 A | 10/1988 | Wusirika |
| 4,814,098 A | 3/1989 | Inada et al. |
| 4,849,210 A | 7/1989 | Widder |
| 5,043,101 A | 8/1991 | Gordon |
| 5,062,991 A | 11/1991 | Siiman et al. |
| 5,069,216 A | 12/1991 | Groman et al. |
| 5,147,841 A | 9/1992 | Wilcoxon |
| 5,248,589 A | 9/1993 | Bose et al. |

(List continued on next page.)

FOREIGN PATENT DOCUMENTS

| | | |
|---|---|---|
| DE | 42 44 354 A1 | 7/1993 |
| EP | 0 049 770 | 4/1982 |
| EP | 0 525 199 | 2/1993 |
| EP | 0 686 448 A2 | 12/1995 |
| EP | 0 586 052 B1 | 7/1997 |
| EP | 0884739 A1 | 12/1998 |
| EP | 0 977 182 A2 | 2/2000 |
| EP | 1 186 659 A1 | 3/2002 |
| WO | 8800060 A1 | 1/1988 |
| WO | 89/11154 | 11/1989 |
| WO | 9305818 A1 | 4/1993 |
| WO | 98/29535 | 7/1998 |
| WO | WO99/46782 * | 9/1999 |
| WO | 9946782 A2 | 9/1999 |
| WO | 00/45171 | 8/2000 |
| WO | 00/71169 A2 | 11/2000 |
| WO | 01/74406 A2 | 10/2001 |

OTHER PUBLICATIONS

Bidan et al. "New Nanocomposites Based on Tailor Dressed Magnetic Particles in a Poypyrrole Matrix" Advanced Materials, VCH Verlagsgesellschaft, Weinheim, Germany vol. 6, No. 2, pp. 152–155 (Feb. 1, 1994).

Ford et al., "Ferritin: Design and Formation of an Iron–Storage Molecule," Phil. Trans. R. Soc. Lond. vol. B304, No. 1121, Feb. 13, 1984, pp. 551–565.

Gider et al. "Classical and Quantum Magnetism in Synthetic Ferritin Proteins" Journal of Applied Physics, American Institute of Physics, New York, vol. 79, No. 8, pp. 5324–5326 (Apr. 15, 1996).

Harris "The Production of Paracrystalline Two–Dimensional Monolayers of Purified Protein Molecules," Micron, Pergamon Press Ltd., United Kingdom, vol. 13, No. 2, pp. 147–168 (1982).

Hong J. et al., "Granular Magnetic Cobalt Metal/Polymer Thin Films System," IEEE Transactions on Magnetics, vol. 32, No. 5, pp. 4475–4477.

(List continued on next page.)

Primary Examiner—Leszek Kiliman
(74) Attorney, Agent, or Firm—Testa, Hurwitz & Thibeault LLP

(57) ABSTRACT

There is disclosed a magnetic fluid medium which comprises a plurality of ferro- or ferri-magnetic particles, each of which particles has a largest dimension no greater than 100 nm, said particles having been prepared by a process which includes a step in which the particles are formed within an organic macromolecular shell.

44 Claims, No Drawings

U.S. PATENT DOCUMENTS

| | | |
|---|---|---|
| 5,262,176 A | 11/1993 | Palmacci et al. |
| 5,304,382 A | 4/1994 | Monzyk |
| 5,328,681 A | 7/1994 | Kito et al. |
| 5,338,617 A | 8/1994 | Workinger et al. |
| 5,358,722 A | 10/1994 | Monzyk |
| 5,429,000 A | 7/1995 | Raj et al. |
| 5,437,892 A | 8/1995 | Nagayama et al. |
| 5,443,813 A | 8/1995 | Hainfeld |
| 5,461,677 A | 10/1995 | Raj et al. |
| 5,491,219 A | 2/1996 | Mann |
| 5,505,996 A | 4/1996 | Nagayama |
| 5,512,332 A | 4/1996 | Liberti et al. |
| 5,543,226 A | 8/1996 | Bobrich et al. |
| 5,547,748 A | 8/1996 | Ruoff et al. |
| 5,552,072 A | 9/1996 | Arase et al. |
| 5,552,229 A | 9/1996 | Brodt et al. |
| 5,574,961 A | 11/1996 | Edelstein et al. |
| 5,690,903 A | 11/1997 | Hainfeld |
| 5,697,902 A | 12/1997 | Goldenberg |
| 5,766,764 A | 6/1998 | Olli et al. |
| 5,843,569 A | 12/1998 | Kaitsu et al. |
| 5,899,220 A * | 5/1999 | Alcocer et al. ............... 137/13 |
| 5,916,539 A | 6/1999 | Pilgrimm |
| 5,948,321 A * | 9/1999 | Hong et al. ................. 252/583 |
| 6,054,495 A | 4/2000 | Markowitz et al. |
| 6,068,785 A | 5/2000 | Raj et al. |
| 6,086,780 A * | 7/2000 | Hong et al. .............. 252/62.52 |
| 6,103,868 A | 8/2000 | Heath et al. |
| 6,120,856 A * | 9/2000 | Liberti et al. ............... 427/550 |
| 6,162,532 A | 12/2000 | Black et al. |
| 6,180,389 B1 | 1/2001 | Douglas |
| 6,254,662 B1 | 7/2001 | Murray et al. |
| 6,262,129 B1 | 7/2001 | Murray et al. |

OTHER PUBLICATIONS

Matsunaga "Synthesis of Nano–Scale Ultrafine Particles Using Biomolecules," Kagaku (Kyoto), vol. 46, Iss. 7, p. 498 (1991).

Meldrum et al., "Magnetoferritn: In Vitro Synthesis of a Novel Magnetic Protein", Science, vol. 257, Jul. 24, 1992, pp. 522–523.

Meldrum, "Nanoscale Synthesis in Organized Assemblies (Ferrtin, Electron Transfer, Magnetotactic Bacteria)," University of Bath (United Kingdom) (1992).

Meldrum et al. "Synthesis of Inorganic Nanophase Materials in Supramolecular Protein Cages," Nature, vol. 349, No. 21, (Feb. 1991).

Moskowitz, et al. "Determination of the Preexponential Frequency Factor for Superparamagnetic Maghemite Particles in Magnetoferritin," J. Geophys. Res., Solid Earth, American Geophysical Union, vol. 102, No. B10 (1997).

Price et al., "Binding of Beryllium and Other Divalent Metal Ions," The Journal of Biological Chemistry, vol. 258, No. 18, Sep. 25, 1983, pp. 10873–10880.

Stefanini et al., "On the Mechanism of Horse Spleen Apoferritin Assembly: A Sedimentation Velocity and Circular Dichroism Study," Biochemistry, vol. 26, No. 7, Apr. 7, 1987, pp. 1831–1837.

Treffry et al., "Spectroscopic Studies on the Binding of Iron, Terbium, and Zinc by Apoferritin," Journal of Inorganic Biochemistry, vol. 21, No. 1 (1984), pp. 9–20.

Wardeska et al., "Metal Ion Complexes of Apoferritin," The Journal of Biological Chemistry, vol. 261, No. 15, May 25, 1986, pp. 6677–6683.

Xu et al. "Collapse of Apo–and Magnetoferritins at the Air–Water Interface," J Colloid Interface Sci, vol. 167, No. 2, pp. 314–319 (1994).

Huang et al., Construction of a Ferritin Reactor: An Efficient Means for Trapping Various Heavy Metal Ions in Flowing Seawater, Journal of Protein Chemistry, vol. 19, No. 6, 2000.

Kenji et al., "Nanometer–Size Structures Fabricated by Bio–Nano–Process", Abstract, Meiji University.

Li et al., "Growth of Single–Walled Carbon Nanotubes From Discrete Catalytic Nanoparticles of Various Sizes", Phys. Chem. B, 105, pp. 11424–11431, 2001.

Warne et al., "Self Assembled Nanoparticulate Co : Pt for Data Storage Applications", IEEE Transactions on Magnetics, vol. 36, No. 5, Sep. 2000.

Yamashita, "Fabrication of a Two–Dimensional Array of Nano–Particles Using Ferritin Molecule", Thin Solid Films, 393, pp. 12–18, 2001.

* cited by examiner

MAGNETIC FLUID

CROSS-REFERENCE TO RELATED APPLICATIONS

This application is the national phase of International (PCT) Patent Application Serial No. PCT/GB00/04517, filed Nov. 27, 2000, published under PCT Article 21(2) in English, which claims priority to and the benefit of United Kingdom Patent Application No. 9927911.9, filed Nov. 25, 1999. This application also claims priority to and the benefit of International (PCT) Patent Application Serial No. PCT/GB97/03152, filed Nov. 17, 1997, published under PCT Article 21(2) in English, now U.S. patent application Ser. No. 09/308,166, which claims priority to and the benefit of United Kingdom Patent Application No. 9623851.4, filed Nov. 16, 1996. This application further relates to U.S. patent application Ser. No. 09/730,117, filed Dec. 5, 2000, which is a continuation of U.S. patent application Ser. No. 09/308, 166. The disclosures of all of these applications are incorporated herein by reference.

This invention relates to a magnetic fluid medium (a ferrofluid) which comprises a suspension of nanoscale ferro- or ferri-magnetic particles dispersed in a carrier liquid. A process for making the ferrofluid is also disclosed.

Ferrofluids are stable suspensions of nanoscale ferro- or ferri-magnetic particles in carrier liquids. The particles are small enough that thermal energy maintains a stable dispersion. However, regardless of the procedure hitherto used for synthesizing ferrofluids, the dispersion is polydisperse (i.e. there is a relatively wide range of particle sizes).

The term "ferromagnetic" is often used in the art to embrace materials which are either "ferromagnetic" or "ferrimagnetic". The present invention may be utilized to prepare fluids containing ferro- or ferri-magnetic nanoscale particles.

According to a first aspect of the present invention, there is provided a magnetic fluid medium which comprises a plurality of ferro- or ferri-magnetic particles, each of which particles has a largest dimension no greater than 100 nm, said particles having been prepared by a process which includes a step in which the particles are formed within an organic macromolecular shell.

Preferably, the ferro- or ferri-magnetic particles have a largest dimension no greater than 50 nm, more preferably no greater than 15 nm.

Preferably, the magnetic fluid medium is monodisperse, by which we mean that the particles in the fluid do not vary in their largest dimension by more than about 10%, preferably by no more than 5%.

Normally, the nanoparticles will be generally spherical in shape, in which case the largest dimension will refer to the diameter of the particle. In some circumstances, other particle morphologies may be established in which case the size of the particles is referred to in terms of the largest dimension.

As a result of the process by which they are formed, each of the ferro- or ferri-magnetic particles is initially at least partially accommodated within an organic macromolecule. In one embodiment, the magnetic fluid medium of the invention comprises the particles still accommodated within the organic macromolecules within which they are formed. In this embodiment, the organic macromolecular shell may be functionalised (see below). In another embodiment, the organic macromolecular shell is removed to leave the nanoparticle itself and in yet a further embodiment, the organic macromolecular shell may be carbonized to provide a carbon layer surrounding a nanoparticle core.

The term macromolecule here means a molecule, or assembly of molecules, which may have a molecular weight of up to 1500 kD, typically less than 500 kD.

The macromolecule should be capable of accommodating or at least partially accommodating the ferro- or ferri-magnetic particle, and may therefore comprise a suitable cavity capable of containing the particle; such a cavity will normally be fully enclosed within the macromolecule. Alternatively, the macromolecule may include a suitable opening which is not fully surrounded, but which nevertheless is capable of receiving and supporting the magnetic particle; for example, the opening may be that defined by an annulus in the macromolecule.

Suitable organic macromolecules which may be used in the invention are proteins having a suitable cavity or opening for accommodating a nanoscale particle. Presently preferred is the protein apoferritin (which is ferritin in which the cavity is empty). However, other suitable proteins include, for example, flagellar L-P rings and virus capsids.

The ferro- or ferri-magnetic material chosen should be one which is capable of being magnetically ordered. It may be a metal, a metal alloy or an M-type or spinel ferrite. The metal, metal alloy or ferrite may contain one or more of the following: aluminium, barium, bismuth, cerium, chromium, cobalt, copper, dysprosium, erbium, europium, gadolinium, holmium, iron, lanthanum, lutetium, manganese, molybdenum, neodymium, nickel, niobium, palladium, platinum, praseodymium, promethium, samarium, strontium, terbium, thulium, titanium, vanadium, ytterbium, and yttrium. The metal, metal alloy or ferrite preferably contains one or more of the following: cobalt, iron and nickel.

In one embodiment of the magnetic fluid medium of the invention, the particles are accommodated or otherwise encased within the organic macromolecule, preferably protein coating, that inhibits aggregation and oxidation, and which also provides a surface which can be functionalised to allow dispersion in a variety of carrier liquids or attachment to contaminants. For example, the surface may be functionalised to render it hydrophobic, thereby allowing dispersion in a non-polar carrier liquid. Another example is to functionalize the surface with, for example, a metal binding ligand to enable the medium to be used in applications for removing metal contaminants from materials such as waste materials.

In this embodiment, the ferro- or ferri-magnetic material chosen is preferably a metal, such as cobalt, iron, or nickel; or a metal alloy; or an M-type ferrite. More preferably, the ferro- or ferri-magnetic material is a metal or a metal alloy.

The present invention most preferably makes use of the iron storage protein, ferritin, whose internal cavity is used to produce nanoscale magnetic particles. Ferritin has a molecular weight of 400 kD. Ferritin is utilised in iron metabolism throughout living species and its structure is highly conserved among them. It consists of 24 subunits which self-assemble to provide a hollow shell roughly 12 nm in outer diameter. It has an 8 nm diameter cavity which normally stores 4500 iron (III) atoms in the form of paramagnetic ferrihydrite. However, this ferrihydrite can be removed (a ferritin devoid of ferrihydrite is termed "apoferritin") and other materials may be incorporated. The subunits in ferritin pack tightly; however there are channels into the cavity at the 3-fold and 4-fold axes. The presently preferred macromolecule for use in the invention is the apoferritin protein which has a cavity of the order of 8 nm in diameter. The ferro- or ferri-magnetic particles to be accommodated within this protein will have a diameter up to about 15 nm in diameter, as the protein can stretch to accommodate a larger particle than one 8 nm in diameter.

Ferritin can be found naturally in vertebrates, invertebrates, plants, fungi, yeasts, bacteria. It can also be produced synthetically through recombinant techniques. Such synthetic forms may be identical to the natural forms, although it is also possible to synthesise mutant forms which will still retain the essential characteristic of being able to accommodate a particle within their internal cavity. The use of all such natural and synthetic forms of ferritin is contemplated within the present invention.

Carrier liquids for ferrofluids are known per se. The carrier liquid may be polar or non-polar. Typical polar carrier liquids include water, lower alcohols such as ethanol, synthetic esters. Water is presently preferred. Typical non-polar carrier liquids which may be used are organic solvents such as heptane, xylene, or toluene, other hydrocarbons, polyglycols, polyphenyl ethers, perfluoropolyethers, silahydrocarbons, halocarbons, or styrene.

The nanoparticles may be prepared by a process in which a suspension of the organic macromolecule, typically in an aqueous medium, is combined with a source of ions of the appropriate metal or metals which is to comprise or consist the nanoparticle. Alternatively, but presently less preferred, the source of metal ions may be present in suspension to which a source of organic macromolecule is added.

The mixture of organic macromolecules and metal ions may be agitated to ensure homogenization.

Where the nanoparticle is to comprise the elemental metal, a reduction is effected, preferably under an inert atmosphere, on the suspension whereby nanoscale metal particles form within the organic macromolecule cavity. Where the nanoparticle is a ferrite, an oxidation is effected whereby the ferrite nanoscale particles are formed within the organic macromolecule cavity. The reduction/oxidation step may be repeated between additions of metal ions (which may be the same or different in each cycle) to build up the nanoparticles.

The resultant suspension may be treated to remove particles not accommodated with a macromolecule, for example by a dialysis technique. If desired, the encased nanoparticles may be isolated, for example by centrifugation prior to suspension in the desired carrier liquid medium.

In some embodiments, the macromolecule casing may be removed to leave the nanoparticle without a coating. For example, where the coating is a protein, this may be denatured through, for example a pH change and the denatured protein material removed by, for example, dialysis or centrifugation.

In other embodiments, the casing may be carbonized to provide a carbon coating on the particles. This may most preferably be accomplished in suspension by laser pyrolysis. However, an alternative is to isolate the particles and then carbonize the protein shell, for example by heating in a furnace, prior to resuspending the particles in the desired carrier liquid.

In a preferred embodiment of the present invention, the organic macromolecule is apoferritin. The following method may be utilized in this preferred embodiment.

The process begins with the removal of the ferrihydrite core from the native.ferritin in aqueous solution, the incorporation of ferro- or ferri-magnetically ordered metal particles by, for example, sodium borohydride reduction of an aqueous metal salt solution into the ferritin cavities, which may be followed by the generation of a narrow size distribution, for example through ultracentrifugation or magnetic separation, and the dispersion of the particles in a carrier liquid.

A metal alloy core may be produced inside the apoferritin protein by sodium borohydride reduction of a selection of water soluble metal salts. Other reduction methods include carbon, carbon monoxide, hydrogen, hydrazine hydrate, or electrochemical. Similar reactions may be used for the production of rare earth/transition metal alloys. Alternatively, a suitable solution may be oxidised to yield an M-type or spinel ferrite core. Oxidation may be chemical or electrochemical to yield the metal ferrite.

In more detail, the protein ferritin is used to enclose a ferro- or ferri-magnetic particle whose largest dimension is limited by the 8 nm inner diameter of ferritin (although as stated above, this is capable of flexing to accommodate particles up to about 15 nm in diameter). The particles are produced first by removing the ferrihydrite core to yield apoferritin. The may be done by dialysis against a buffered sodium acetate solution under a nitrogen flow. Reductive chelation using, for example, thioglycolic acid may be used to remove the ferrihydrite core. This may be followed by repeated dialysis against a sodium chloride solution to completely remove the reduced ferrihydrite core from solution.

Once the apoferritin is produced, magnetic particles are incorporated in the following ways. The first is by reducing a metal salt solution in the presence of apoferritin. This is performed in an inert atmosphere to protect the metal particles from oxidation which would lessen their magnetic properties. A combination of metal salts in solution can also be reduced to generate alloys, or precursor materials. Another method is to oxidise a combination of an iron (II) salt and another metal salt. This gives a metal ferrite particle which does not suffer negatively from oxidation. The metal salts which are beneficial include salts of aluminium, barium, bismuth, cerium, chromium, cobalt, copper, dysprosium, erbium, europium, gadolinium, holmium, iron, lanthanum, lutetium, manganese, molybdenum, neodymium, nickel, niobium, palladium, platinum, praseodymium, promethium, samarium, strontium, terbium, thulium, titanium, vanadium, ytterbium, and yttrium.

While the production procedure detailed uses native horse spleen ferritin, this invention should not be seen as limited to that source. Ferritin can be found in vertebrates, invertebrates, plants, fungi, yeasts, bacteria, or even produced through recombinant techniques.

After the production of the ferro- or ferri-magnetic particles, the aqueous suspension can be used directly as a magnetic fluid medium (ferrofluid). However, other carrier liquids can be used through extraction of the particles or their passivation. Passivation or extraction may be performed by coating the protein in a surfactant or by derivitising it with organic chains. However, the invention should not be seen as limited to these methods. Other carrier liquids which may be used are organic solvents such as heptane, xylene, or toluene, hydrocarbons, synthetic esters, polyglycols, polyphenyl ethers, perfluoropolyethers, silahydrocarbons, halocarbons, or styrene. Methods for the preparation of ferrofluids are described in U.S. Pat. No. 6,068,785, the content of which is hereby incorporated by reference. A number of books and references also discuss the science of magnetic fluids, including their preparation.

These references include: Magnetic Fluid Applications Handbook, editor in-chief: B. Berkovsky, Begell House Inc., New York (1996); Ferrohydrodynamics, R. E. Rosensweig, Cambridge University Press, New York (1985); Ferromagnetic Materials-A Handbook on the Properties of Magnetically Ordered Substances, editor E. P. Wohlfarth, Chapter 8, North-Holland Publishing Company, New York and "Proceedings of the 7th International Conference on Magnetic Fluids", Journal of Magnetism and Magnetic Materials, Vol. 149, Nos. 1–2 (1995).

In this invention, one of the advantages of ferritin being employed to fabricate a magnetic particle through encapsulation, is that it can be used to select particles of a uniform size. This narrow size distribution enhances the monodispersity of the fluid, and allows for a more uniform response to an applied field and an enhanced stability of the dispersion.

When generating ferrofluids for various applications, it is desirable to address a range of responsiveness and temperatures. As ferrofluids with higher magnetization (or those which can be used at higher temperatures) may be desirable, those which respond to temperature by causing their magnetic properties to lessen dramatically can be undesirable. Such a change can occur when particles become superparamagnetic, which is the standard state of a ferrofluid. Superparamagnetic particles are those which have permanent magnetic dipole moments, but the orientations of the moments with respect to the crystallographic axes fluctuate with time. Superparamagnetism depends on the volume, temperature, and anisotropy or the material used. Via energy considerations, one can derive an equation relating these quantities. The volume at which a particle or region becomes superparamagnetic ($V_p$) is given by: $V_p$=25 kT/K, where k is Boltsman's constant, T the temperature in degrees Kelvin, and K the anisotropy constant of the material. Using this formula, it is possible to determine the temperature at which a particle or region becomes superparamagnetic (the "blocking temperature") for a given material at a fixed volume. As an example, the fixed volume is 8 nm in ferritin. If a cobalt metal particle with only crystalline anisotropy (that value being $45 \times 10^5$) is a sphere with a diameter of 8 nm, the blocking temperature is 353° K. By tuning the materials incorporated into ferritin, a wide range of responsiveness and temperatures can be addressed.

The main application areas for the magnetic fluid medium of the invention are sealing, heat transfer, damping, separation, security coding, as a magnetic carrier for inks in printing, a transducer, a pressure sensor, in a loudspeaker, as an optical switch and for the formation of ordered structures.
Sealing The ferrofluid of the invention may be used for sealing a bearing, such as those used in computer-disc-drive applications as described in, for example, U.S. Pat. Nos. 4,673,997 and 4,692,826, the content of each of which is hereby incorporated by reference. The ferrofluid is used to seal a rotating shaft through the use of an annular magnetic pole and opposite on a shaft which magnetically confine the ferrofluid between them. The ferrofluid acts as a liquid gasket allowing free rotation of the shaft.
Heat Transfer The ferrofluid of the invention may be used as a cooling medium as detailed in U.S. Pat. No. 5,462,685 the content of which is hereby incorporated by reference. One way to cool a device is to draw a ferrofluid towards it using magnetic fields. As the ferrofluid nears the device and warms above its curie point, it loses a significant portion of its magnetisation and becomes displaced by the cooler, more magnetic fluid. A convective circuit is thus formed and the device cooled.

Damping

The ferrofluid of the invention may be used as a damping medium as detailed in U.S. Pat. No. 4,123,675 the content of which is hereby incorporated by reference. The viscosity of a ferrofluid may be affected by the presence of an external magnetic field. One example is a suspension shaft or spring which is confined to a chamber filled with a ferrofluid. Upon the application of an external magnetic field, the viscosity of the ferrofluid is enlarged and the freedom of movement of the shaft or spring lessened. In this way, the external magnetic field may form part of a circuit that actively damps vibrations or movements of the shaft or spring.
Security Coding/Printing Ink For security coding, the ferrofluid of this invention may be used as a magnetic ink for printing and storing information, or may provide a unique magnetic signature for the marking of bank notes or other important documents or items. Also, by dispersing the magnetic fluid in coloured carrier liquids, it can be used as a printing ink which is deposited through electromagnetic means.
Transducer The ferrofluid of the invention may be used in a ferrofluid transducer as described, for example, in U.S. Pat. No. 4,361,879 the content of which is hereby incorporated by reference. For example, an underwater sound generator composed of a ferrofluid in accordance with the invention may be contained within a toroidal container which has a rigid bottom and top and elastic cylindrical side walls. A coil of wire links the toroidal container and is adapted to be connected to a dc bias source to produce a biasing magnetic field, HBIAS, which drives the magnetization of the ferrofluid well into saturation. Two oppositely wound coils of wire respectively link the inner side wall and the outer side wall and are adapted to be connected in series to an ac signal source to produce a time-varying magnetic field, HAC, which modulates HBIAS. The wires are equally spaced in the volume occupied by the ferrofluid. The gradient of HAC in the radial direction provides the time-varying force on the ferrofluid. The resulting ferrofluid motion in the radial direction is transmitted through the outer elastic side wall to supply acoustic motion to the surrounding water.
Pressure Sensor The ferrofluid of the invention may be used in a ferrofluid pressure sensor as described, for example, in U.S. Pat. No. 5,429,000 the content of which is hereby incorporated by reference. For example, a differential pressure sensor includes a ferrofluid sensing element, or slug, that changes position in a tapered magnetic field in response to a pressure differential. The ferrofluid slug is contained in a tube and moves within the tapered magnetic field, which is perpendicular to the longitudinal axis of the tube. The field has a maximum flux density at its centre and tapers off in both axial directions from its centre. In response to a pressure differential of zero, the slug is centred in the field. In response to a non-zero pressure differential, the slug moves to the position in the field where the net magnetic forces equal the pressure differential. The position of the slug is sensed by sensing elements which produce output signals that vary according to the position of the slug. In one embodiment the sensing elements are pickup coils that are positioned to encompass the range of movement of one end of the slug, or are a pair of pickup coils positioned, respectively, to encompass the range of movement of the two ends of the slug. The ferrofluid slug thus acts as a movable core for the pickup coil(s). As the ferrofluid slug moves, it changes the relative inductances of the pickup coils. The one coil or the pair of coils are connected in a bridge circuit, which produces an output signal that varies according to the changing inductances, and thus the pressure differential.

Loudspeaker

The ferrofluid of the invention may be used in a loudspeaker as described, for example, in U.S. Pat. No. 5,461,677 the content of which is hereby incorporated by reference. More specifically, the air gap in a loudspeaker may be filled with a ferrofluids of the invention. The ferrofluid transfers heat from the voice coil and also provide damping for the movement of the coil, thereby reducing distortion in the speaker and smoothing its frequency response. For further explanation, see W. Bottenberg, L. Melillo and K. Raj, "The Dependence of Loudspeaker Design Parameters on the Properties of Magnetic Fluids," Journal of Audio Engineering Society, Volume 28, January/February 1980, pp. 17–25. Ferrofluids are particularly useful in speakers that move their voice coils relatively large distances, such as woofers and sub-woofers which respond to low frequencies. See, for example, L. Melillo and K. Raj, "Ferrofluids as a Means of Controlling woofer Design Parameters," Journal of Audio Engineering Society, Volume 29, No. 3, 1981 March pp. 132–139.

Optical Switch

The ferrofluid of the invention may be used as an optical switch as described, for example, in U.S. Pat. No. 4,384,761 the content of which is hereby incorporated by reference. In more detail, a controllable magnetic field is used to influence the position or shape or density distribution of a ferrofluid so that the ferrofluid causes or prevents the coupling of light between optical paths either by physically causing movement of a waveguide (e.g., optical fiber) or by itself physically moving into or out of a coupling region between optical paths.

Ordered Structures

The ferrofluid of the invention may be used to prepare ordered structures as described, for example, in U.S. Pat. Nos. 5,948,321 and 6,086,780, the content of each of which is hereby incorporated by reference. A thin film of the ferrofluid is subjected to an external magnetic field to generate ordered one dimensional structures or two dimensional lattices in thin films of these ferrofluid compositions in response to externally applied magnetic fields. A variety of magnetic-optical devices can be constructed that use the ordered structures to diffract, reflect, and polarize light in a controlled and predictable manner. These devices include color displays, monochromatic light switches, and tunable wavelength filters.

When the particles are encapsulated in a protein with functional groups, antibodies or other charged moieties can be attached in order to magnetically extract contaminants from a waste stream.

In all application areas, this invention exploits its beneficial properties of having tuneable magnetic properties, monodispersity, and the ability to exist in many carrier liquids.

The invention will now be illustrated by reference to the accompanying, non-limiting examples.

EXAMPLE 1

This example illustrates the preparation of apoferritin from horse spleen ferritin. Apoferritin was prepared from cadmium-free native horse spleen ferritin by dialysis (molecular weight cut-off of 10–14 kD) against sodium acetate solution (0.2 M) buffered at pH 5.5 under a nitrogen flow with reductive chelation using thioglycolic acid (0.3 M) to remove the ferrihydrite core. This was followed by repeated dialysis against sodium chloride solution (0.15 M) to completely remove the reduced ferrihydrite core from solution.

EXAMPLE 2

This example illustrates the preparation of iron metal within apoferritin. The apoprotein was added to a deaerated AMPSO/sodium chloride solution (0.1/0.4 M) buffered at pH 8.5 to give an approximate 1 mg/ml working solution of the protein which was heated to 60° C. A deaerated iron (II) [for example, as the acetate salt] solution (1 mg/ml) was added incrementally such that the total number of atoms added was approximately 500 atoms/apoprotein molecule. This was allowed to stir at room temperature for one day in an inert atmosphere. This was followed by reduction of the iron (II) salt with sodium borohydride to iron (0) metal. The final product yielded a solution of iron particles, each surrounded by a ferritin shell.

EXAMPLE 3

This example illustrates the preparation of cobalt metal within apoferritin. The apoprotein was added to a deaerated AMPSO solution (0.05 M) buffered at pH 8.5 to give an approximate 1 mg/ml working solution of the protein which was heated to 45° C. A deaerated cobalt (II) [for example, as the acetate salt] solution (0.1 M) was added incrementally such that the total number of atoms added was approximately 500 atoms/apoprotein molecule. This was allowed to stir at this temperature for one hour in an inert atmosphere. This was followed by reduction of the cobalt (II) salt with sodium borohydride to cobalt (0) metal. The final product yielded a solution of cobalt particles, each surrounded by a ferritin shell.

EXAMPLE 4

This example illustrates the preparation of a metal alloy such as yttrium cobalt ($YCo_5$) within apoferritin. The metal alloy followed the same procedure as Example 2, but using a 1:5 ratio of yttrium (III) [for example, as the acetate salt] to cobalt (II) [for example, as the acetate salt]. The final product yielded a solution of yttrium cobalt particles, each surrounded by a ferritin shell.

EXAMPLE 5

This example illustrates the preparation of a metal alloy such as cobalt platinum (CoPt) within apoferritin. The metal alloy followed the same procedure as Example 3, but using a 1:1 ratio of platinum (II) [for example, as the acetate salt] to cobalt (II) [for example, as the acetate salt] and a higher pH (9.0). The final product yielded a solution of cobalt platinum particles, each surrounded by a ferritin shell.

EXAMPLE 6

This example illustrates the preparation of a metal ferrite such as cobalt ferrite ($CoO\cdot Fe_2O_3$) within apoferritin. The apoprotein was added to a deaerated AMPSO/sodium chloride solution (0.1/0.4 M) buffered at pH 8.5 to give an approximate 1 mg/ml working solution of the protein which was heated to 60° C. A deaerated solution of cobalt (II) [for example, as the acetate salt] and iron (II) [for example, as the ammonium sulphate salt] in a ratio of 1:2 was added incrementally and selectively oxidised using trimethylamine. The final product yielded a solution of cobalt ferrite particles, each surrounded by a ferritin shell.

EXAMPLE 7

This example illustrates the incorporation of the product from Examples 2–6 into a carrier liquid other than the natural aqueous one. The product of Examples 2–4 was mixed 1:100 with oleic acid as a surfactant and stirred for 24 hours, dried in a rotovac apparatus, then resuspended in kerosene.

What is claimed is:

1. A magnetic fluid medium, comprising a plurality of magnetic particles, each of said magnetic particles havinz a largest dimension no greater than about 100 nm, said plurality of magetic pticicles prepared by a process comprising the step of forming at least one of said magnetic particles within a shell of at least one organic macromolecule, wherein said at least one organic macromolecule is a molecule, or assembly of molecules, having a molecular weight of up to 1500 kD and wherein said at least one of said magnetic particles comprises a metal or a metal alloy.

2. The magnetic fluid medium of claim 1, wherein each of said magnetic particles has a largest dimension no greater than about 50 nm.

3. The magnetic fluid medium of claim 1, wherein each of said magnetic particles has a largest dimension no greater than about 15 nm.

4. The magnetic fluid medium of claim 1, wherein said magnetic particles vary in their largest dimension by no more than about 10%.

5. The magnetic fluid medium of claim 1, wherein said magnetic particles vary in their largest dimension by no more than about 5%.

6. The magnetic fluid medium of claim 1, wherein at least one of said magnetic particles is accommodated within the organic macromolecule within which it is formed.

7. The magnetic fluid medium of claim 1, wherein said shell of said at least one organic macromolecule has been removed thereby forming an uncoated nanoscale particle.

8. The magnetic fluid medium of claim 1, wherein said shell of said at least one organic macromolecule has been carbonized thereby providing a carbon layer surrounding a nanoscale particle core.

9. A magnetic fluid medium, comprising a plurality of magetic particles, each of said magnetic particles having a largest dimension no greater than about 100 nm, said plurality of magnetic particles prepared by a process comprising the step of forming at least one of said magnetic particles within a shell of at least one organic macromolecule, wherein said at least one organic macromolecule is a protein having a cavity for accommodating a nanoscale particle therein and wherein said at least one of said magnetic particles comprises a metal or a metal alloy.

10. The magnetic fluid medium of claim 9, wherein said protein is an apoferritin.

11. The magnetic fluid medium of claim 1, wherein said magnetic particles are selected from the group consisting of ferromagnetic particles, ferrimagnetic particles, and a mixture thereof.

12. An integrated magnetic fluid seal disposed between a rotatable shaft and a bearing assembly comprising a plurality of magnetic particles, each of said magnetic particles having a largest dimension no greater than about 100 nm, said plurality of magnetic particles prepare by a process comprising the step of forming at least one of said magnetic particles within a shell of at least one organic macromolecule, wherein said at least one organic macromolecule is a molecule, or assembly of molecules, having a molecular weight of up to 1500 kD.

13. A fluid medium for cooling of an electromagnetic device producing an external magnetic field and having an operating temperature, said medium comprising a plurality of magnetic particles, each of said magnetic particles having a largest dimension no greater than about 100 nm, said plurality of magnetic particles prepared by a process comprising the step of forming at least one of said magnetic particles within a shell of at least one organic macromolecule, wherein said at least one organic macromolecule is a molecule, or assembly of molecules, having a molecular weight of up to 1500 kD.

14. A fluid medium for cooling of an electromagnetic device producing an external magnetic field and having an operating temperature, said medium comprising a plurality of magnetic particles, each of said magnetic particles having a largest dimension no greater than about 1100 nm said plurality of magnetic particles prepared by a process comprising the step of forming at least one of said magnetic particles within a shell of at least one organic macromolecule, wherein a concentration of said plurality of magnetic particles therein produces a bulk saturation magnetization of said medium of at least 50 Gauss.

15. The medium of claim 13 wherein the Curie temperature of said plurality of magnetic particles exceeds the average operating temperature of said electromagnetic device, and wherein said medium loses substantial magnetization at the average operating temperature.

16. The medium of claim 13 wherein the Curie temperature of said plurality of magnetic particles exceeds the maximum operating temperature of said electromagnetic device, and wherein said medium loses substantial magnetization at the maximum operating temperature.

17. A damping medium for absorbing energy, said damping medium having a predetermined viscosity controllable by an application of an external magnetic field and comprising a plurality of magnetic particles, each of said magnetic particles having a largest dimension no greater than about 100 nm, said plurality of magnetic particles prepared by a process comprising the step of forming at least one of said magnetic particles within a shell of at least one organic macromolecule, said at least one organic macromolecule comprising a molecule, or assembly of molecules, having a molecular weight of up to 1500 kD.

18. A method for creating a unique magnetic marking on a substrate, said method comprising the steps of providing a magnetic medium comprising a plurality of magnetic particles, each of said magnetic particles having a largest dimension no greater than about 100 nm, said plurality of magnetic particles prepared by a process comprising the step of forming at least one of said magnetic particles within a shell of at least one organic macromolecule; and applying said medium to said substrate.

19. A fluid pressure sensor comprising a magnetic fluid medium disposed in a tube having a first end and a second end, said magnetic fluid medium displaceable in response to a pressure differential between the first and the second end of said tube; said magnetic fluid medium comprising a plurality of magnetic particles, each of said magnetic particles having a largest dimension no greater than about 100 nm, said plurality of magnetic particles prepared by a process comprising the step of forming at least one of said magnetic particles within a shell of at least one organic macromolecule, wherein said at least one organic macromolecule is a molecule, or assembly of molecules, having a molecular weight of up to 1500 kD.

20. A method for reducing distortion in a loudspeaker having a voice coil, the method comprising:

providing a magnetic fluid medium comprising a plurality of magnetic particles, each of said magnetic particles having a largest dimension no greater than about 100 nm, said plurality of magnetic particles prepared by a process comprising the step of forming at least one of said magnetic particles within a shell of at least one organic macromolecule, said at least one organic macromolecule comprising a molecule, or assembly of molecules, having a molecular weight of up to 1500 kD; and disposing said magnetic fluid adjacent to said voice coil thereby transferring heat therefrom and providing damping therefor.

21. An optical switch comprising at least two optical fibers having coupling of light therebetween; and a magnetic fluid medium disposed proximal to said at least two optical fibers and comprising a plurality of magnetic particles, each of said magnetic particles having a largest dimension no greater than about 100 nm, said plurality of magnetic particles prepared by a process comprising the step of forming at least one of said magnetic particles within a shell of at least one organic macromolecule, said at least one organic macromolecule comprising a molecule, or assembly of molecules, having a molecular weight of up to 1500 kD, wherein at least one of;

(a) positioning of said magnetic fluid relative to said optical fibers, or (b) at least one physical property of said magnetic fluid medium is alterable in response to an application of an external magnetic field thereto, thereby causing obstruction of said coupling of light.

22. A magneto-optical device comprising a magnetic fluid medium comprising a plurality of magnetic particles, each of said magnetic particles having a largest dimension no greater than about 100 nm, said plurality of magnetic particles prepared by a process comprising the step of forming at least one of said magnetic particles within a shell of at least one organic macromolecule, said at least one organic macromolecule comprising a molecule, or assembly of molecules, having a molecular weight of up to 1500 kD, said magnetic fluid medium forming an ordered crystalline array in response an application of an external magnetic field thereto.

23. The magnetic fluid medium of claim 1, wherein said at least one organic macromolecule is a molecule, or assembly of molecules, having a molecular weight of up to 500 kD.

24. The magnetic fluid medium of claim 9, wherein said magnetic particles are selected from the group consisting of ferromagnetic particles, ferrimagnetic particles, and a mixture thereof.

25. The magnetic fluid medium of claim 9, wherein each of said magnetic particles has a largest dimension no greater than about 50 nm.

26. The magnetic fluid medium of claim 9, wherein said magnetic particles vary in their largest dimension by no more than about 10%.

27. The magnetic fluid medium of claim 9, wherein at least one of said magnetic particles is accommodated within the cavity of the protein.

28. The magnetic fluid medium of claim 9, wherein said shell of said at least one organic macromolecule has been removed thereby forming an uncoated nanoscale particle.

29. The magnetic fluid medium of claim 9, wherein said shell of said at least one organic macromolecule has been carbonized thereby providing a carbon layer surrounding a nanoscale particle core.

30. A magnetic fluid medium, comprising a plurality of magnetic particles, each of said magnetic particles having a largest dimension no greater than about 100 nm, said plurality of magnetic particles prepared by a process comprising the step of forming at least one of said magnetic particles within a shell of at least one organic macromolecule, wherein said at least one organic macromolecule is a molecule, or assembly of molecules, having a molecular weight of up to 1500 kD and wherein said at least one of said magnetic particles comprises an M-type ferrite or a spinel ferrite.

31. The magnetic fluid medium of claim 30, further comprising a carrier liquid.

32. The magnetic fluid medium of claim 30, wherein said at least one organic macromolecule is a molecule, or assembly of molecules, having a molecular weight of up to 500 kD.

33. A magnetic fluid medium, comprising a plurality of magnetic particles, each of said magnetic particles having a largest dimension no greater than about 100 nm, said plurality of magnetic particles prepared by a process comprising the step of forming at least one of said magnetic particles within a shell of at least one organic macromolecule, wherein said at least one organic macromolecule is a protein having a cavity for accommodating a nanoscale particle therein and wherein said at least one of said magnetic particles comprises an M-type ferrite or a spinel ferrite.

34. The magnetic fluid medium of claim 33, wherein said protein is an apoferritin.

35. The magnetic fluid medium of claim 33, further comprising a carrier liquid.

36. The magnetic fluid medium of claim 33, wherein each of said magnetic particles has a largest dimension no greater than about 50 nm.

37. The magnetic fluid medium of claim 33, wherein said magnetic particles vary in their largest dimension by no more than about 10%.

38. The magnetic fluid medium of claim 33, wherein at least one of said magnetic particles is accommodated within the cavity of the protein.

39. The magnetic fluid medium of claim 33, wherein said shell of said at least one organic macromolecule has been removed thereby forming an uncoated nanoscale particle.

40. The magnetic fluid medium of claim 33, wherein said shell of said at least one organic macromolecule has been carbonized thereby providing a carbon layer surrounding a nanoscale particle core.

41. A magnetic fluid medium, comprising a plurality of magnetic particles, each of said magnetic particles having a largest dimension no greater than about 100 nm, said plurality of magnetic particles prepared by a process comprising the step of forming at least one of said magnetic particles within a shell of at least one organic macromolecule, wherein said magnetic particles vary in their largest dimension by no more than about 10% and wherein said at least one of said magnetic particles comprises a metal or a metal alloy.

42. A method for separating solid phase from a liquid suspension, the method comprising;

providing a magnetic fluid medium comprising a plurality of magnetic particles, each of said magnetic particles having a largest dimension no greater than about 100 nm, said plurality of magnetic particles prepared by a process comprising the step of forming at least one of said magnetic particles within a shell of at least one organic macromolecule, said at least one organic macromolecule comprising a molecule, or assembly of molecules, having a molecular weight of up to 1500 kD, adding said magnetic fluid medium to said suspension, and extracting said solid phase from said suspension.

43. A method of claim 42, wherein said at least one organic macromolecule is an apoferritin.

44. A method of claim 42, wherein said at least one magnetic particle comprises a metal binding ligand disposed at the surface thereof.

* * * * *